United States Patent
Welch

(10) Patent No.: US 7,153,280 B2
(45) Date of Patent: Dec. 26, 2006

(54) INCOMPETENT CERVIX AIDE

(76) Inventor: Robert A. Welch, 8400 N. Ridge Rd., Canton, MI (US) 48187-1112

( * ) Notice: Subject to any disclaimer, the term of this patent is extended or adjusted under 35 U.S.C. 154(b) by 192 days.

(21) Appl. No.: 10/924,035

(22) Filed: Aug. 23, 2004

(65) Prior Publication Data
US 2005/0021049 A1 Jan. 27, 2005

Related U.S. Application Data

(62) Division of application No. 10/293,831, filed on Nov. 13, 2002, now Pat. No. 6,905,472.

(51) Int. Cl.
*A61B 5/117* (2006.01)
*A61B 5/103* (2006.01)

(52) U.S. Cl. ..................... 600/591

(58) Field of Classification Search ............ 600/41, 600/588, 591, 37, 29–32; 128/830; 251/5; 446/224
See application file for complete search history.

(56) References Cited

U.S. PATENT DOCUMENTS

| | | | |
|---|---|---|---|
| 183,602 A | 10/1876 | Strubell | |
| 3,254,650 A | 6/1966 | Collito | |
| 3,404,682 A | 10/1968 | Waldron | |
| 3,741,216 A * | 6/1973 | Yosowitz et al. | 128/830 |
| 4,203,432 A | 5/1980 | Koch | |
| 4,401,534 A | 8/1983 | Goepp et al. | |
| 4,543,949 A | 10/1985 | Goepp et al. | |
| 5,108,408 A | 4/1992 | Lally | |
| 5,807,281 A | 9/1998 | Welch | |
| 5,810,710 A | 9/1998 | Burgos | |
| 5,928,249 A | 7/1999 | Saadat et al. | |
| 5,931,775 A | 8/1999 | Smith | |
| 5,980,534 A | 11/1999 | Gimpelson | |
| 6,419,646 B1 | 7/2002 | Baxter-Jones | |
| 6,423,000 B1 | 7/2002 | Berry | |

* cited by examiner

*Primary Examiner*—Max F. Hindenburg
*Assistant Examiner*—Brian Szmal
(74) *Attorney, Agent, or Firm*—Dickinson Wright PLLC

(57) ABSTRACT

Two embodiments of an annular cervical ring have an internal diameter 14 for surrounding the cervix 12. Each embodiment also includes a tightening device 16 for decreasing the internal diameter 14 to tighten the annular ring down around the cervix 12 to hold the cervix 12 closed.

4 Claims, 1 Drawing Sheet

INCOMPETENT CERVIX AIDE

RELATED APPLICATIONS

This application is a divisional of application Ser. No. 10/293,831, filed Nov. 13, 2002 now U.S. Pat. No. 6,905,472.

BACKGROUND OF THE INVENTION

1. Field of the Invention
2. Description of the Prior Art

A small percentage of pregnant women miscarry or deliver prematurally because of a weak cervix. These women frequently do not experience pain during this premature dilation of the cervix. This painless cervical dilatation is known as "incompetent cervix".

SUMMARY OF THE INVENTION AND ADVANTAGES

The present invention surrounds and holds the cervix closed during pregnancy to reduce the chance for either a miscarriage or premature delivery.

In accordance with the subject invention the cervix is held closed by placing an internal diameter of an annular cervical ring around the cervix in the vagina of a woman and decreasing the internal diameter of the cervical ring to tighten cervical ring down around the cervix. The cervix is held closed for an extended period of time sufficient for a normal pregnancy to full term by a tightening device for decreasing the internal diameter around the cervix.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1:
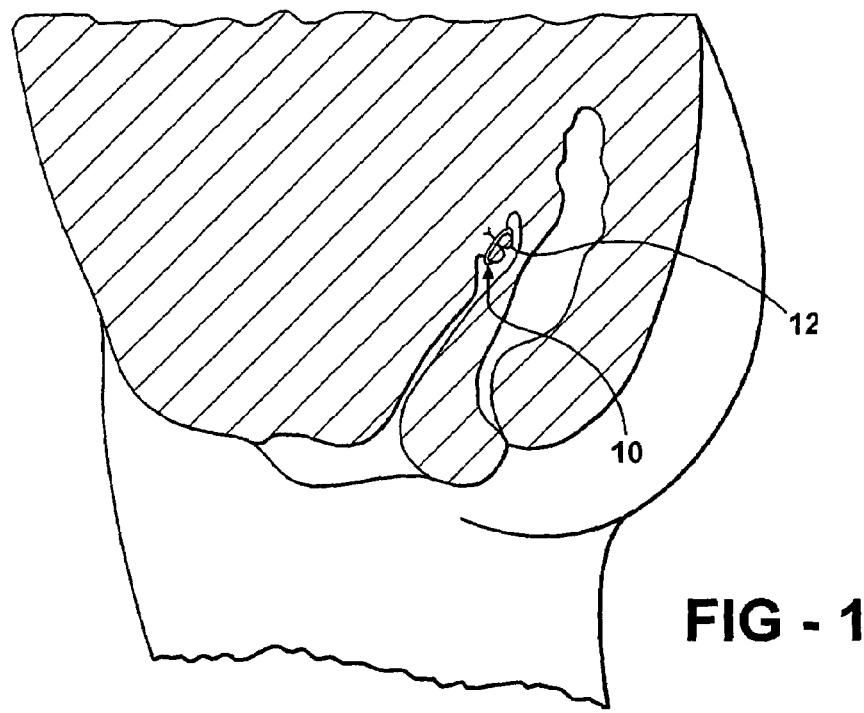
FIG. 1 is a fragmentary cross sectional view of a human female with the invention disposed on the cervix.
Figure 2:
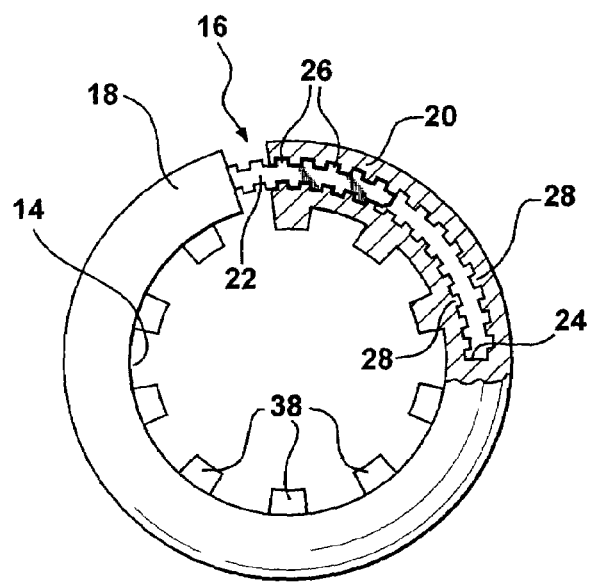
FIG. 2 is a side view of one embodiment of the invention.
Figure 3:
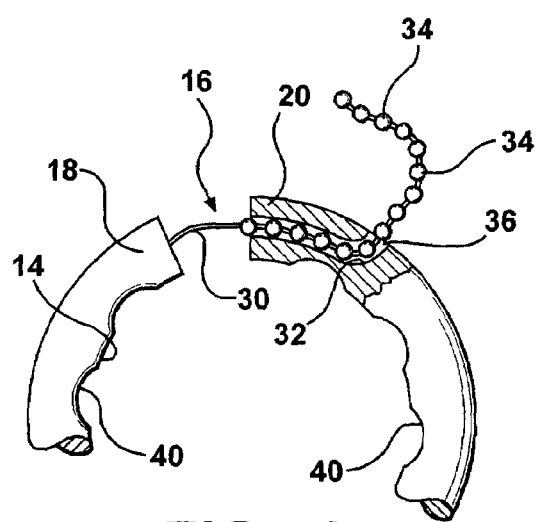
FIG. 3 is a fragmentary side view, partially cut away and in cross section, of another embodiment of the invention.

Referring to the Figures, wherein like numerals indicate like or corresponding parts throughout the several views, a cervical ring for surrounding the exterior of the cervix 12 is generally shown at 10 in FIG. 1 with two different embodiments respectively shown in FIGS. 2 and 3.

Each embodiment includes an annular cervical ring having an internal diameter 14 for surrounding the cervix 12. Each embodiment also includes a tightening device, generally shown at 16, for decreasing the internal diameter 14 to tighten the annular ring down around the cervix 12 to hold the cervix 12 closed.

The tightening device 16 includes a separation in the ring to define first 18 and second 20 portions separated along the circumference of the ring with the first portion 18 telescoped into the second portion 20 for decreasing the circumference of the internal diameter 14. The tightening device 16 of the embodiment of FIG. 2 includes a tongue 22 integrally formed with the first portion 18 of the ring and extending into a cavity 24 in the second portion 20 of the ring. A plurality of ratcheting teeth 26, 28 interconnect the first 18 and second 20 portions for mechanically holding the portions 18 and 20 together. More specifically, a first plurality of ratcheting teeth 26 extend radially outwardly from the tongue 22 of the first portion 18 and a second plurality of ratcheting teeth 28 extend radially inwardly from the interior of the cavity 24 in the second 20 portion of the ring. The ratcheting teeth 26, 28 are shown as square in shape but as is readily apparent the teeth may take many shapes so long as the tongue 22 may be forced into the cavity 24 and held there by the teeth. The tightening device 16 of the embodiment of FIG. 3 includes a string 30 integrally formed with the first portion 18 of the ring and extending into a passage 32 in the second portion 20 of the ring. A plurality of balls 34 are formed integrally with the string 30 and are spaced along the string 30 to interconnect the first 18 and second 20 portions for mechanically holding the portions 18 and 20 together. More specifically, the balls 34 extend radially outwardly from the string 30 of the first portion 18 and a retaining lip 36 surrounds the exit of the passageway 32 in the second 20 portion of the ring to prevent the string 30 from being pulled out of the passageway 32. This is a familiar tightening feature used in straps used to close trash bags. As will be appreciated various mechanical devices may be used to tighten the ring about the cervix.

As shown in the embodiment of FIG. 2, the ring may include projections 38 extending radially from the internal diameter 14 for defining spaces therebetween for facilitating blood flow. Alternatively, the ring may include scallops 40 in the internal diameter 14 to define projections therebetween for facilitating blood flow.

As will be appreciated, the invention provides a method for holding the cervix 12 closed comprising the steps of placing an internal diameter 14 of an annular cervical ring around the cervix 12 in the vagina of a woman, decreasing the internal diameter 14 of the cervical ring to tighten cervical ring down around the cervix 12, and holding the cervix 12 closed for an extended period of time. The ring may be removed from the cervix 12 with an appropriate instrument, e.g., an instrument to cut the ring, as the ring is made of plastic material.

The method includes the telescoping of the first portion 18 of the cervical ring into the second portion 20 of the cervical ring to decrease the internal diameter 14. Also included is the ratcheting of the first portion 18 into the second portion 20 and mechanically holding the portions 18, 20 together.

Obviously, many modifications and variations of the present invention are possible in light of the above teachings. The invention may be practiced otherwise than as specifically described within the scope of the appended claims, wherein that which is prior art is antecedent to the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the incentive novelty exercises its utility. In addition, the reference numerals in the claims are merely for convenience and are not to be read in any way as limiting.

What is claimed is:

1. A cervical ring adapted for surrounding the exterior of the cervix (12) comprising;
    an annular cervical ring having an internal diameter (14) for surrounding the cervix (12), and a tightening device (16) including a first portion (18) and a second portion (20) of said ring with said first portion (18) telescoped into said second portion (20) for decreasing said internal diameter (14) to tighten said annular ring down around the cervix (12) to hold the cervix (12) closed.

2. An assembly as set forth in claim 1 including ratcheting teeth (26, 28 and 34, 36) interconnecting said first (18) and second (20) portions for mechanically holding said portions together.

3. An assembly as set forth in claim 2 wherein said ratcheting teeth extend radially from one of said first (18) and second (20) portions of said ring and are disposed within said circumference of said ring.

4. An assembly as set forth in claim 1 including projections extending radially from said internal diameter (14) for defining spaces therebetween for facilitating blood flow.

* * * * *